(12) United States Patent
Kubota et al.

(10) Patent No.: US 11,135,501 B2
(45) Date of Patent: Oct. 5, 2021

(54) GENERATION DEVICE AND GENERATION METHOD

(71) Applicant: FUJITSU LIMITED, Kawasaki (JP)

(72) Inventors: Kazumi Kubota, Kawasaki (JP); Kazuya Kawashima, Fukuoka (JP); Tsuyoshi Matsumoto, Fukuoka (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 16/367,363

(22) Filed: Mar. 28, 2019

(65) Prior Publication Data

US 2019/0217184 A1     Jul. 18, 2019

Related U.S. Application Data

(63) Continuation of application No. PCT/JP2016/080153, filed on Oct. 11, 2016.

(51) Int. Cl.
*A63B 71/06*     (2006.01)
*G16H 20/30*     (2018.01)
*G06F 7/24*     (2006.01)

(52) U.S. Cl.
CPC .......... *A63B 71/0619* (2013.01); *A63B 71/06* (2013.01); *G06F 7/24* (2013.01); *G16H 20/30* (2018.01)

(58) Field of Classification Search
CPC ........... A63B 71/06; A63D 15/20; A63F 7/32; G06F 7/24
See application file for complete search history.

(56) References Cited

U.S. PATENT DOCUMENTS 6,190,287 B1    2/2001   Nashner
2005/0130803 A1    6/2005   Rastegar et al.
(Continued)

FOREIGN PATENT DOCUMENTS

JP    2009-112731    5/2009
JP    2009-219828    10/2009
(Continued)

OTHER PUBLICATIONS

Journal of Applied Physiology, Apr. 18, 2012, Cameron J. Mitchell, Resistance exercise load does not determine training-mediated hypertrophic gains in young men, p. 76 (Year: 2012).*
(Continued)

*Primary Examiner* — Omkar A Deodhar
(74) *Attorney, Agent, or Firm* — Fujitsu Patent Center

(57) ABSTRACT

A generation device includes a memory, and a processor coupled to the memory and configured to receive first performance composition including a plurality of skills, refer to load information representing a load on each body part when a skill is performed and calculate a load value indicating a total of the load applied to a performer who performs the first performance composition, refer to scoring rules that stipulate scores based on difficulty of skills and calculate a performance score indicating a total of scores of the plurality of skills included in the first performance composition, and based on the load information and the scoring rules, generate second performance composition according to performance rules that stipulate composition of the skills, the second performance composition leading to a score higher than the performance score and reducing the load value.

15 Claims, 17 Drawing Sheets

(56) References Cited

U.S. PATENT DOCUMENTS

2016/0030804 A1  2/2016  Mizuochi et al.
2016/0199693 A1  7/2016  Vermilyea et al.

FOREIGN PATENT DOCUMENTS

JP      2010-264088      11/2010
WO      2012/071548 A1   5/2012

OTHER PUBLICATIONS

International Search Report attached with the Written Opinion of the International Searching Authority, mailed in connection with PCT/JP2016/080153 and dated Dec. 27, 2016, with partial English translation (9 pages).
EESR—Extended European Search Report dated Aug. 20, 2019 from corresponding European Patent Application No. 16918780.4.
US2005/130803A1 cited in the EESR was previously submitted in IDS filed on Mar. 28, 2019.
EPOA—Office Action of European Patent Application No. 16918780.4 dated Mar. 11, 2020. ** References cited in the EPOA were previously submitted in the IDS filed on Mar. 28, 2019 and Sep. 12, 2019.

* cited by examiner

FIG. 3

| PART | HEAD | RIGHT HAND | RIGHT ARM | RIGHT UPPER ARM | CHEST | ABDOMEN | LOWER ABDOMEN | RIGHT THIGH | RIGHT LEG | RIGHT FOOT |
|---|---|---|---|---|---|---|---|---|---|---|
| MASS | 4 | 2 | 4 | 6 | 11 | 8 | 9 | 6 | 3 | 3 |

FIG. 4

| SKILL NAME | RIGHT WRIST | LEFT WRIST | RIGHT UPPER ARM | LEFT UPPER ARM |
|---|---|---|---|---|
| SCISSOR SKILL A | 5 | 25 | 5 | 5 |
| CIRCLES SKILL B | 10 | 45 | 30 | 35 |
| TURNING SKILL C | 20 | 20 | 20 | 20 |
| ... | ... | ... | ... | ... |

FIG. 5

| SKILL NAME | GROUP AND DIFFICULTY | LOAD (RIGHT WRIST, LEFT WRIST, RIGHT UPPER ARM, AND LEFT UPPER ARM) | POSTURE (STARTING AND ENDING) | SUCCESS RATE |
|---|---|---|---|---|
| CIRCLES SKILL A | GROUP I, DIFFICULTY 0.4 | 5, 25, 5, 5 | STARTING: FRONT SUPPORT, MIDDLE ENDING: LEGS CROSSED, MIDDLE | 95% |
| ⋮ | ⋮ | ⋮ | ⋮ | ⋮ |

FIG. 6

| PRECEDING SKILL / FOLLOWING SKILL | SCISSOR SKILL A | CIRCLES SKILL B | CIRCLES SKILL C | ... |
|---|---|---|---|---|
| SCISSOR SKILL A | – | G(5) | H(0) | ... |
| CIRCLES SKILL B | X(5) | – | Q(10) | ... |
| CIRCLES SKILL C | Z(0) | Y(15) | – | ... |
| ... | ... | ... | ... | ... |

FIG. 8

INPUT SKILL TO PERFORM
AND PRESS PERFORM
ESTIMATION BUTTON

| ORDER | SKILL NAME | DIFFICULTY | GROUP |
|---|---|---|---|
| 1 | BACK SCISSOR TO HANDSTAND | D | I |
| 2 | E FLOP | E | IV |
| 3 | D COMBINE | D | IV |
| 4 | LOOP | B | II |
| 5 | MAGYAR | D | III |
| 6 | SIVADO | D | III |
| 7 | DIRECT STOCKLI B | B | IV |
| 8 | WENDE | B | IV |
| 9 | KEHR BACKWARD TRAVEL | B | III |
| 10 | WENDE BACKWARD TRAVEL WITH HANDSTAND 3/3 TRAVEL AND ONE TWIST DISMOUNT | E | V |

PERFORM ESTIMATION

| ORDER | SKILL NAME | DIFFICULTY | GROUP | DIFFICULTY ADDED POINT |
|---|---|---|---|---|
| 1 | BACK SCISSOR TO HANDSTAND | D | I | 0.4 |
| 2 | E FLOP | E | IV | 0.5 |
| 3 | D COMBINE | D | IV | 0.4 |
| 4 | LOOP | B | II | 0.2 |
| 5 | MAGYAR | D | III | 0.4 |
| 6 | SIVADO | D | III | 0.4 |
| 7 | DIRECT STOCKLI B | B | IV | 0.2 |
| 8 | WENDE | B | IV | 0.2 |
| 9 | KEHR BACKWARD TRAVEL | B | III | 0.2 |
| 10 | WENDE BACKWARD TRAVEL WITH HANDSTAND 3/3 TRAVEL AND ONE TWIST DISMOUNT | E | V | 0.5 |

| RIGHT WRIST JOINT LOAD | 7.5 | K(Nm) |
| LEFT WRIST JOINT LOAD | 8.4 | K(Nm) |
| SCORE (D SCORE) | 5.9 | |

FIG. 10B

| ORDER | SKILL NAME | DIFFICULTY | GROUP | DIFFICULTY ADDED POINT |
|---|---|---|---|---|
| 1 | MIKULAK | D | I | 0.4 |
| 2 | E FLOP | E | IV | 0.5 |
| 3 | D COMBINE | D | IV | 0.4 |
| 4 | LOOP | B | II | 0.2 |
| 5 | MAGYAR | D | III | 0.4 |
| 6 | SIVADO | D | III | 0.4 |
| 7 | DIRECT STOCKLI B | B | IV | 0.2 |
| 8 | WENDE | B | IV | 0.2 |
| 9 | KEHR BACKWARD TRAVEL | B | III | 0.2 |
| 10 | WENDE BACKWARD TRAVEL WITH HANDSTAND 3/3 TRAVEL AND ONE TWIST DISMOUNT | E | V | 0.5 |

| | K(Nm) |
|---|---|
| RIGHT WRIST JOINT LOAD | 6.9 |
| LEFT WRIST JOINT LOAD | 8.4 |
| SCORE (D SCORE) | 5.9 |

GENERATION DEVICE AND GENERATION METHOD

CROSS-REFERENCE TO RELATED APPLICATION

This application is a continuation application of International Application PCT/JP2016/080153 filed on Oct. 11, 2016 and designated the U.S., the entire contents of which are incorporated herein by reference.

FIELD

The embodiments discussed herein are related to a generation device, and a generation method.

BACKGROUND

In competitions or the like in which a player performs a series of skills and referees mark, success of a skill with higher difficulty or a degree of perfection greatly influences a higher score or a higher rank. For example, men's artistic gymnastics includes six events and women's artistic gymnastics four events. In both men's and women's artistic gymnastics, in the events other than the valting horse, one performance includes ten or more skills sequentially performed by a player. Scoring rules define criteria for a skill type, a group, a number, and fulfillment, and stipulate that a same skill is counted only once to add a point in one performance, or that only top ten skills on a score rank are considered for marking. Consequently, players are requested to incorporate and perform a great number of skills with higher difficulty in the above specified range.

In recent years, there is known a technique that assists sports athletes or the like, by using 3D sensing to acquire information on a posture or a motion of a person or the like. For example, this technique is utilized to capture the motion or the like of a gymnast when he/she performs a skill during practice and allow the him/her to check the degree of perfection of the skill.

However, the foregoing technique may not assist performance composition that alleviates burdens on a body, or the like. For example, in the pommel horse, a gymnast performs in a three-dimensional motion of a complicated CIRCLES skill involving twisting or changing of a body orientation while holding two pommels. In this motion, not only the total body weight but also a kinetic load involved in the twisting or a rotational motion is applied to player's wrist joints. In some cases, force equivalent to twice the body weight is applied in an instant. Since a gymnast's body makes a three-dimensionally complicated motion as described above, and a body-build or a skill motion varies for each player, it is difficult to accurately estimate the load on the joints or muscles.

The following is a reference document.
[Document 1] Japanese Laid-open Patent Publication No. 2010-264088.

SUMMARY

According to an aspect of the invention, a generation device includes a memory, and a processor coupled to the memory and configured to receive first performance composition including a plurality of skills, refer to load information representing a load on each body part when a skill is performed and calculate a load value indicating a total of the load applied to a performer who performs the first performance composition, refer to scoring rules that stipulate scores based on difficulty of skills and calculate a performance score indicating a total of scores of the plurality of skills included in the first performance composition, and based on the load information and the scoring rules, generate second performance composition according to performance rules that stipulate composition of the skills, the second performance composition leading to a score higher than the performance score and reducing the load value.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 3 is a diagram of an example of information stored in a body information DB;

FIG. 4 is a diagram of an example of information stored in a load DB;

FIG. 5 is a diagram of an example of information stored in a performance data DB;

FIG. 6 is a diagram of an example of information stored in a connection action DB;

FIG. 8 is an explanatory diagram of input of performance composition;

FIGS. 10A and 10B are explanatory diagrams of a generation example of the performance composition that minimizes load;

DESCRIPTION OF EMBODIMENTS

A generation program, a generation method, and a generation device according to the present invention are described hereinafter in detail. Note that this embodiment does not limit the present disclosure.

Embodiment 1

[Description of a Measurement Device]

Figure 1:
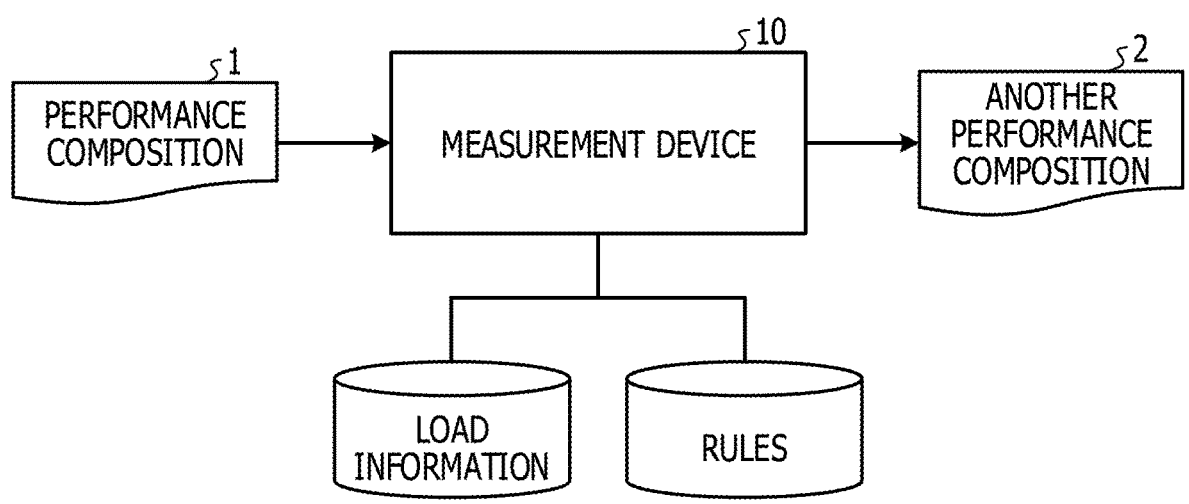
FIG. 1 is a diagram of a measurement device according to Embodiment 1.

FIG. 1 is a diagram of a measurement device 10 according to Embodiment 1. The measurement device 10 is an example of a computer such as a server, a tablet terminal, a smart phone or the like, and an example of a generation device. Using a 3D (Three Dimensions) scanner, the measurement device 10 gets hold of mass, a center of gravity or the like of each body part by measuring a physical constitution of a performer. In addition, the measurement device 10 registers scoring rules for each of competition events in a database, so that a skill type, a group, a score, a number of times, and marking criteria are usable as indexes for the rules. The measurement device 10 also calculates in advance a physical quantity of a load applied on each of joints and muscles of each time a skill is performed, by measuring a posture or a motion of a body and applying the posture or the motion to a skeleton model.

Specifically, the measurement device 10 stores load information that associates the skill of the artistic gymnastics such as the pommel horse, the vaulting horse, the horizontal bar, or the like with burdens on the body when the skill is performed. For example, the load information indicates the motion of each joint during a performance and the load thereby applied by tracking the posture or the motion of the performer through 3D sensing.

In addition, the measurement device 10 stores rules stipulated on the skill type, the group, the number, and fulfillment. By way of example, the rules stipulate that a point is added only once to a same skill in one performance or that top ten skills on a score rank are targets of marking, or the like.

When receiving performance composition 1 generated according to the rules and including a plurality of skills, such a measurement device 10, while observing the rules, determines another performance composition 2 with a higher score and smaller load, from some performance candidates in which a combination of skills differ.

For example, the measurement device 10 refers to the load information and calculates a load value which is a total of the load applied on the performer who performs the performance composition 1. Then, the measurement device 10 refers to the rules, which are the scoring rules, and calculates a performance score which is a total of scores of a plurality of skills included in the performance composition 1. Then, based on the load information and the rules, the measurement device 10 generates another performance composition 2 leading to a score higher than the performance score of the performance composition 1 and reducing the load value of the performance composition 1, in accordance with the rules that define the performance rules.

As a result, the measurement device 10 may maintain the scores and observe the rules, and assist the performance composition that alleviates the burdens on the body. Note that in the embodiment, although description is given with the pommel horse of the artistic gymnastics as an example, the measurement device is not limited to this, and may be applied to any other competitions where players perform a series of skills and referees mark. Examples of the other competitions include other events of the artistic gymnastics, figure skating, rhythmic gymnastics, cheerleading, or the like.

[Functional Configuration]

Figure 2:
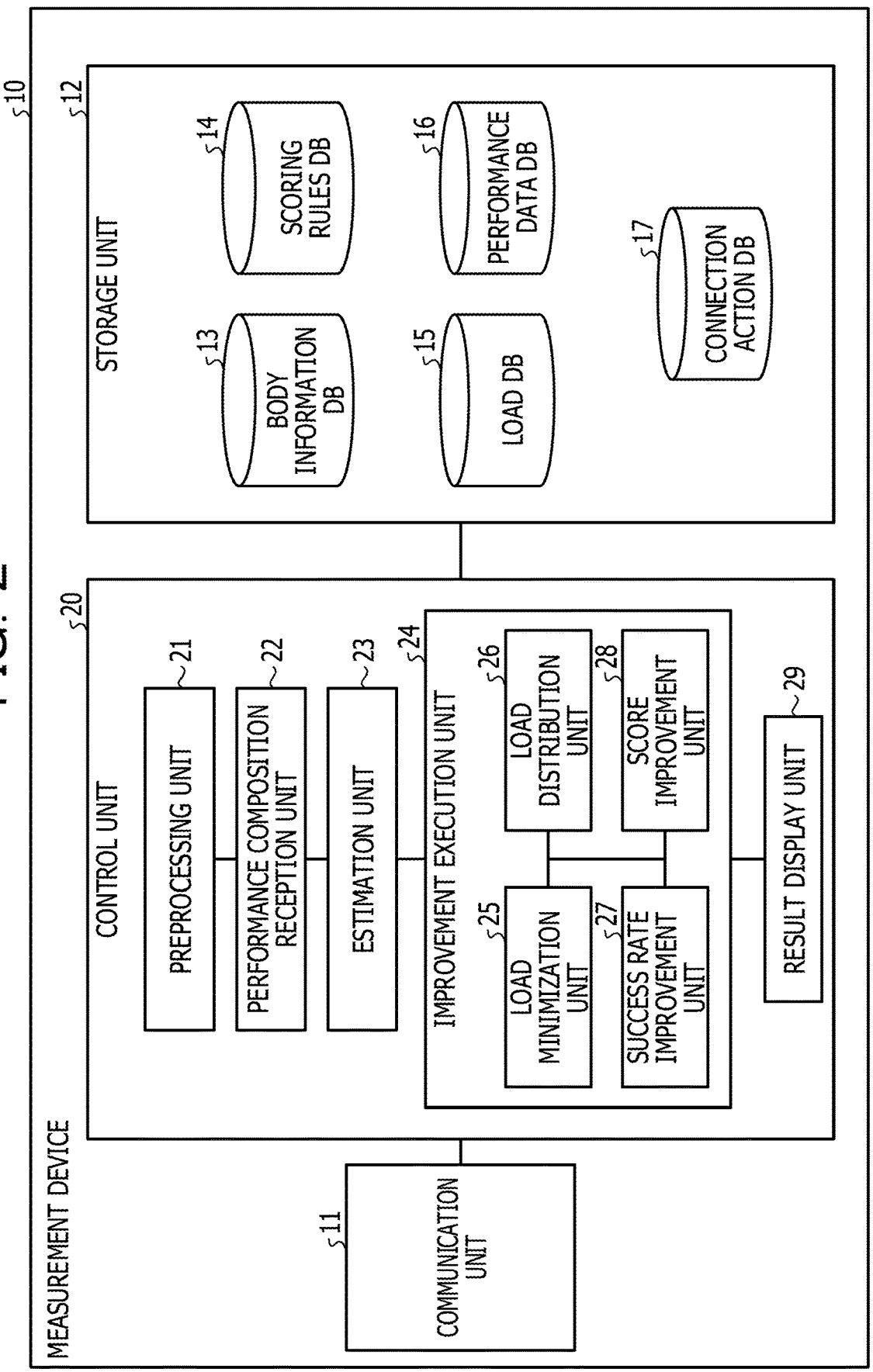
FIG. 2 is a functional block diagram of a functional configuration of the measurement device according to Embodiment 1.

FIG. 2 is a functional block diagram of a functional configuration of the measurement device 10 according to Embodiment 1. As illustrated in FIG. 2, the measurement device 10 includes a communication unit 11, a storage unit 12, and a control unit 20. Note that the functional configuration illustrated here is an example, and the measurement device 10 may include, for example, a display unit that displays various types of information or an input unit that receives input of each piece of information.

The communication unit 11 is a communication interface that controls communications with other devices. The communication unit 11 receives the performance composition or the like from an external device, for example, and inputs the performance composition to the control unit 20. The communication unit 11 also transmits new performance composition to the external device.

The storage unit 12 is an example of a storage device that stores a program or data and is a memory or a hard disk, for example. The storage unit 12 stores a body information DB 13, a scoring rule DB 14, a load DB 15, a performance data DB 16, and a connection action DB 17.

The body information DB 13 is a database that stores mass of a body part of each performer. Information stored here may be the mass of each part of the performer having the average system or may be the mass of each body part that is measured for each performer by a 3D scanner.

FIG. 3 is a diagram of an example of information stored in the body information DB 13. As illustrated in FIG. 3, the body information DB 13 associates and stores "the part and the mass". The "part" represents a portion of the performer's body and the "mass" is the physical quantity (Kg) of the part. An example of FIG. 3 illustrates the mass of a head being "4" and the mass of a right hand being "2", or the like.

The scoring rule DB 14 is a database that stores the rules defined for the skill type, the group, the number, and the fulfillment. Specifically, the scoring rule DB 14 stores the rules stipulating that the point is added only once to the same skill in one performance or that the top ten skills on the score rank are the targets of marking.

For example, the rules stored in the scoring rule DB 14 stipulate that the skills listed in a difficulty point table specified in advance in the artistic gymnastics are to be performed, that at least one skill in each of the skill groups specified in the difficulty point table is to be included, and that the same skill may be repeated, but no D score is involved, or the like.

The load DB 15 is a database that stores the load information which associates the skill and the burdens on the body when the skill is performed. Information stored here is the load information of each performer. In addition, the information stored here may be past information or information estimated in advance, or may be information identified by the 3D sensing.

FIG. 4 is a diagram of an example of information stored in the load DB 15. As illustrated in FIG. 4, the load DB 15 stores the load information that associates the "Skill Name, Right Wrist, Left Wrist, Right Upper Arm, and Left Upper Arm". The "Skill Name" is a name of skills of the pommel horse. The "Right Wrist" represents the load applied on the right wrist when the skill is performed and the "Left Wrist" represents the load applied on the left wrist when the skill is performed. The "Right Upper Arm" represents the load applied on the right upper arm when the skill is performed and the "Left Upper Arm" represents the load applied on the left upper arm when the skill is performed. Note that the load information is a value representing a fatigue degree per unit time, for example. When the value is multiplied, the value represents a cumulative fatigue degree. The larger numeric value means that the fatigue degree per unit time is high and the load that causes fatigue is high.

An example of FIG. 4 illustrates that when a scissor skill A is performed, the load applied on the right wrist is 5, the load applied on the left wrist is 25, the load applied on the right upper arm is 5, and the load applied on the left upper arm is 5. A gymnast's body makes a three-dimensionally complicated motion, and a body-build or a skill motion varies for each player. Thus, the load applied on the joints or the muscles is accurately estimated by the 3D sensing and the estimated load is stored in the load DB 15.

The performance data DB 16 is a database that stores information on the skills performed by performers on a performer-by-performer basis. FIG. 5 is a diagram of an example of the information stored in the performance data DB 16. As illustrated in FIG. 5, the performance data DB 16 associates and stores the "Skill Name, Group and Difficulty, Load (Right Wrist, Left Wrist, Right Upper Arm, and Left Upper Arm), Posture (Starting and Ending), and Success Rate".

The "Skill Name" stored here represents the name of the skill of the pommel horse. The "Group and Difficulty" is information identifying a group to which the skill belongs and the difficulty. Here, the group represents the skills of the pommel horse grouped by the starting skill, the dismount, the TURNING skill, or the like, according to the international standard. Note that the foregoing scoring rules define the performance rules that one skill from each of the groups is to be performed, that as the starting skill, the skill in a predetermined group (Group I, for example) is to be performed, that as the dismount, the skill in the predetermined group (Group V, for example) is to be performed, or the like. The difficulty is the internationally standardized difficulty, and the points to be added are determined for each of A to H, for example. For example, for the difficulty D, it is determined that "Difficulty D, Point Added: 0.4", for the difficulty B, it is determined that "Difficulty B, Point Added: 0.2", or the like. The higher the difficulty is, the more points are added.

The "Load (Right Wrist, Left Wrist, Right Upper Arm, and Left Upper Arm)" represents the load to be applied on the performer when the performer performs the skill identified by the skill name. The information may be identified from the load DB 15. The "Posture (Starting and Ending)" is information representing a starting posture and an ending posture of the skill. The information may be identified in advance because the skill motion is determined. The "Success Rate" represents the success rate of the skill identified by the skill name when the skill is performed by the performer during practice or during a match. The information may be calculated from the past record in advance.

An example of FIG. 5 illustrates that a circles skill A belongs to Group I and is of the difficulty D whose difficulty added point is 0.4. The example also illustrates that for the circles skill A, when the skill is performed, the load of 5 is applied on the right wrist, the load of 25 on the left wrist, the load of 5 on the right upper arm, and the load of 5 on the left upper arm, and that the success rate is 95%. In addition, the circles skill A means that the performer starts in a front support state at the middle of the horse and ends at the middle of the horse with his legs crossed.

The connection action DB 17 is a database that stores connection action information representing a load of a connection action performed by the performer when the performer shifts the performance from a first skill to a second skill. FIG. 6 is a diagram of an example of information stored in the connection action DB 17. The information stored in FIG. 6 is registered in advance.

As illustrated in FIG. 6, the connection action DB 17 stores weight associated with a "preceding skill" and a "following skill" and taking into consideration a name and the load of the connection action, the preceding skill being performed first and the following skill being performed subsequently. An example 6 indicates that when a circles skill B is performed following the scissor skill A, a connection action X with the load of "5" is performed. Note that the load here is also synonymous with the load information in FIG. 4.

The control unit 20 is a processing unit that controls the entire measurement device 10 and is a processor, for example. The control unit 20 includes a preprocessing unit 21, a performance composition reception unit 22, an estimation unit 23, an improvement execution unit 24, and a result display unit 29. Note that the preprocessing unit 21, the performance composition reception unit 22, the estimation unit 23, the improvement execution unit 24, and the result display unit 29 are an example of an electronic circuit such as a processor or an example of a process performed by the processor.

The preprocessing unit 21 is the processing unit that calculates in advance body information of the performer or the load applied on the performer, and the calculated body information and load in the corresponding DB. Specifically, the preprocessing unit 21 uses the 3D scanner to measure the physical constitution and identifies the mass or the center of gravity of each body part. In addition, the preprocessing unit 21 records actual performance of a series of skills included in the performance composition and performed by the performer. Using the 3D sensing, the preprocessing unit 21 measures the posture or the motion of the body, applies the posture or the motion to the skeleton model, and calculates the physical quantity of the load applied on each of the joints and muscle every time the skill is performed.

For example, the preprocessing unit 21 measures the performer's body with the 3D scanner, calculates the mass of each part of the performer's body, and stores the mass in the body information DB 13. The preprocessing unit 21 analyzes the performer's performance with the 3D sensing and identifies the posture of the body during the performance and the weight on each part of the body in such a posture.

Figure 7:
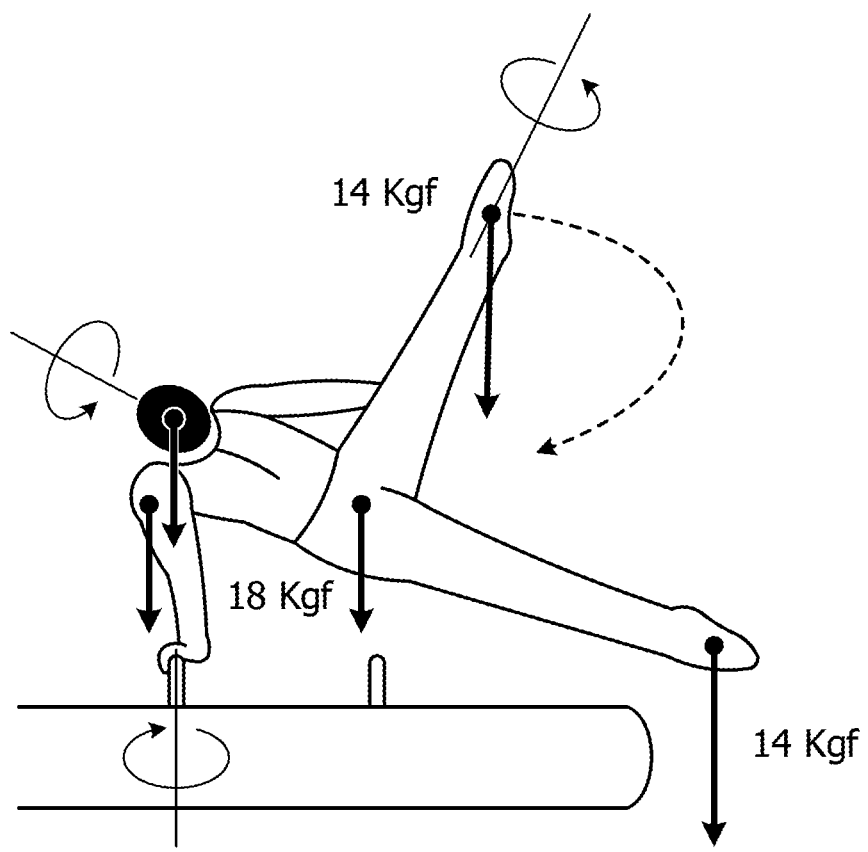
FIG. 7 is an explanatory diagram of a relation of a skill posture and an exercise volume of a body part.

FIG. 7 is an explanatory diagram of a relation between a skill posture and an exercise volume of the body part. With the 3D sensing using a 3D radar sensor, the preprocessing unit 21 acquires the exercise volume (Kgf: kilogram weight) of each part during the performance illustrated in FIG. 7. As illustrated in FIG. 7, the preprocessing unit 21 acquires information that the exercise volumes of 18 Kgf, 14 Kgf, and 14 Kgf are respectively applied to the hips, the right foot, and the left foot during the performance of the scissor skill A.

In this manner, the preprocessing unit 21 acquires the exercise volume applied to each body part when each skill is performed and the exercise volume applied to each body part when each connection action is performed. Then, from the acquired exercise volume and the body information illustrated in FIG. 3, the preprocessing unit 21 calculates the load applied on each body part (load information) for each skill and each connection action, using a publicly known calculating formula or the like. Then, the preprocessing unit 21 stores the calculated load in the load DB 15 or the connection action DB 17.

In addition, the preprocessing unit 21 identifies the posture (starting and ending) of each skill with the 3D sensing. Then, the preprocessing unit 21 identifies the group or the difficulty of each skill from the scoring rule DB 14 or the like. Thereafter, the preprocessing unit 21 associates the group, the difficulty, the posture, the load stored in the load DB 15 or the like and stores in the performance data DB 16. Note that for the load or the like may be adopted an average value of same performances performed more than once when the exercise volume is identified using the 3D sensing.

In addition, the success rate when the performances are done more than once is calculated and may be stored in the performance data DB 16.

The performance composition reception unit 22 is the processing unit that receives the performance composition 1 generated by the performer or the like and including the plurality of skills. Specifically, the performance composition reception unit 22 displays an input screen on a display or the like and receives a performance order and the skills to be performed. At this time, the performance composition reception unit 22 may also receive the difficulty and the group from the performer or the like, and may identify them from the performance data DB 16 by using the received skill name and automatically input them.

FIG. 8 is an explanatory diagram of input of the performance composition 1. The performance composition reception unit 22 displays the input screen illustrated in FIG. 8 and receives ten performances for the "Order, Skill Name, Difficulty, and Group". In an example of FIG. 8, the performance composition reception unit 22 receives input of "1. Back Scissor to Handstand, D, I", "2. E Flop, E, IV", or the like and displays a result of the reception. In the input screen displayed here, a "Perform Estimation" button for performing estimation of the load of the performance composition 1 is displayed, in addition to the received performance composition 1. Note that the performance composition reception unit 22 is an example of a reception unit.

The estimation unit 23 is the processing unit that estimates the load or the score (D score) of the performer when the performer performs the performance composition that is conceived and generated by the performer or the like. Specifically, for the performance composition 1 received by the performance composition reception unit 22, when the "Perform Estimation" button in the input screen illustrated in FIG. 8 is selected, the estimation unit 23 performs the estimation of the performance composition and displays a estimation result.

For example, the estimation unit 23 acquires from the performance data DB 16 or the scoring rule DB 14 or the like the difficulty (difficulty added point) of each of the ten skills received by the performance composition reception unit 22 and calculates a total value of the difficulty of all the skills as the score (D score) of the inputted performance composition. In addition, the estimation unit 23 acquires the load (right wrist, left wrist, right upper arm, and left upper arm) of each of the ten skills from the load DB 15 or the performance data DB 16. Subsequently, the estimation unit 23 calculates the load on each of the right wrist, the left wrist, the right upper arm, and the left upper arm when each skill is performed or the total value of the load. Then, the estimation unit 23 displays the score (D score), the load on the right wrist, the load on the left wrist, the load on the right upper arm, and the load on the left upper arm for the inputted performance composition 1.

Figure 9:
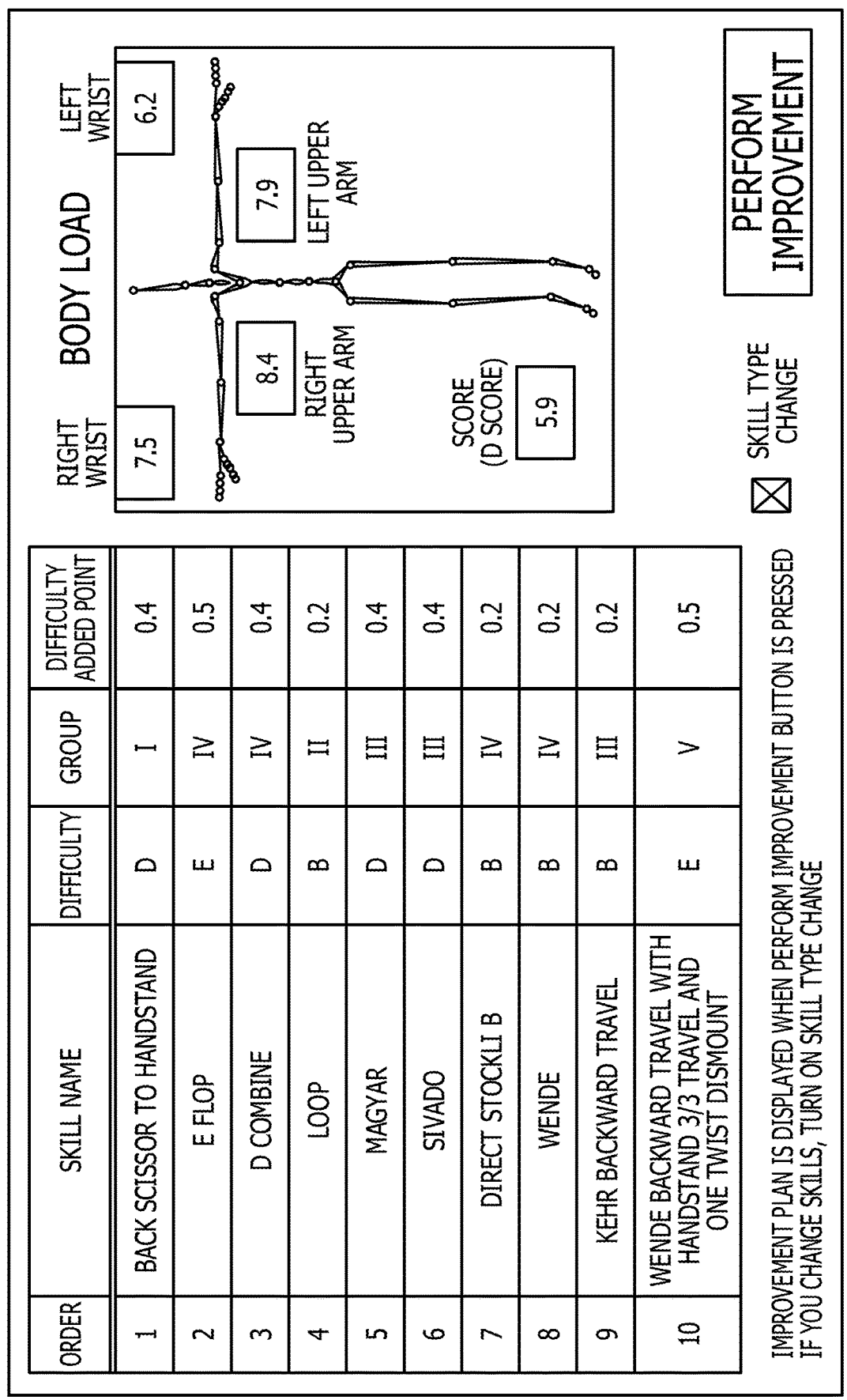
FIG. 9 is an explanatory diagram of an estimation result.

FIG. 9 is an explanatory diagram of the estimation result. As illustrated in FIG. 9, the estimation unit 23 displays a estimation result display screen including the difficulty added point and the score (D score) of each skill inputted, and the body load (load on the right wrist, load on the left wrist, load on the right upper arm, and load on the left upper arm). As illustrated in FIG. 9, the estimation unit 23 calculates and displays the "D score (5.9)", the D score being the points by adding the difficulty added point of the respective first to tenth skills, the total value of the difficulty added points of all the skills "0.4+0.5+0.4+0.2+0.4+0.4+0.2+0.2+0.2+0.5=3.4", and a reference point, or the like. In addition, as illustrated in FIG. 9, the estimation unit 23 calculates and displays a total of the load applied on each part of the body when each of the first to the tenth skills is performed. Moreover, for each of the skills, the estimation unit 23 calculates and displays the total value "7.5" of the load applied on the right wrist when the skill is performed, the total value "6.2" of the load applied on the left wrist, the total value "8.4" of the load applied on the right upper arm, and the total value "7.9" of the load applied on the left upper arm. Note that the average value may replace the total value.

Note that the estimation unit 23 displays such that the load may be seen visually, by displaying the body load information on a human schematic diagram like FIG. 9, or the like. In addition, the estimation result screen also displays a "Perform Improvement" button and a "Change Skill Type" button, "Perform Improvement" button for causing selection to be made of whether or not an improvement proposal is desired, or "Change Skill Type" button for causing the selection to be made of whether or not a skill type change is desired.

The improvement execution unit 24 includes a load minimization unit 25, a load distribution unit 26, a success rate improvement unit 27, and a score improvement unit 28, and is the processing unit that generates the improvement proposal (performance composition 2) for the performance composition 1 inputted by the performer or the like. Specifically, in the estimation screen illustrated in FIG. 9, when an "Perform Improvement" button is selected with the "Perform Improvement" button selected, the improvement execution unit 24 generates different performance composition 2 from the standpoint of minimizing the load, from the standpoint of distributing the load, from the standpoint of improving the success rate, and from the standpoint of increasing the score. At this time, the improvement execution unit 24 generates the different performance composition 2, while observing the complicated scoring rules stored in the scoring rule DB 14. In addition, if the "Change Skill Type" is not selected, the improvement execution unit 24 generates the different performance composition 2 from the standpoint of distributing the load.

The load minimization unit 25 is the processing unit that generates different performance composition 2 that leads to the score higher than the performance score of the performance composition 1 and reduces the total load of the performance composition 1, according to the scoring rule that for each group, the skill is to be performed at least once or more, or the like. Specifically, for the skill specified for each order of the performance composition 1, the load minimization unit 25 searches the performance data DB 16 for whether or not there is a skill that belongs to the same group and has the difficulty added point higher than the difficulty added point of the specified skill. Then, if the corresponding skill is searched, the load minimization unit 25 generates the different performance composition 2 in which the specified skill is replaced by the searched skill.

Figure 10A:

FIGS. 10A and 10B are explanatory diagrams of a generation example of the performance composition that minimizes load. An example of FIGS. 10A and 10B illustrates a changed example of the skill of the order 1. As illustrated in FIGS. 10A and 10B, the load minimization unit 25 detects presence of the skill "Mikulak" that belongs to Group I of the Back Scissor to Handstand of the order 1, and in which the load on the right wrist is smaller by 0.6 only than the load of the Back Scissor to Handstand and other loads are same, of the skills of the Back Scissor to Handstand with the difficulty of D or higher. As a result, the load minimization unit 25 generates the different performance composition 2 in which the Back Scissor to Handstand of the order 1 is changed to Mikulak.

Then, the load minimization unit 25 outputs to the result display unit 29 content (order or skill name, or the like) of the performance composition 2 in which the skills are changed, the load on each part when the performance composition 2 is performed, the total load, or the like. In this manner, the load minimization unit 25 generates the different performance composition 2 with the small load, without changing the skill group or the difficulty that are originally set. Therefore, the load minimization unit 25 may propose the performance composition with the small load, while observing the scoring rules.

Note that if more than one different skill with the small load is detected for one order, the load minimization unit 25 may select the skill with the highest difficulty, and may select any skill if the difficulty of the corresponding different skills is same. In addition, if the different skills with the small load are detected in a plurality of the orders of one performance composition 1, the load minimization unit 25 may change the skills of all detected orders, may change any number of skills, may change to the skill the success rate of which is a threshold value or higher, or may select and change so that the load is smaller than the predefined threshold value. Note that the load minimization unit 25 is an example of a first calculation unit, a second calculation unit, and a generation unit.

The load distribution unit 26 is the processing unit that changes the order of the respective skills in the inputted performance composition 1 to generate the performance composition 2, so that there are a smaller number of parts where the load is continuously high. In addition, the load distribution unit 26 is the processing unit that changes the order of the respective skills in the inputted performance composition 1 to generate performance composition 2, so that there are a small number of the connection actions. Then, similarly to the load minimization unit 25, the load distribution unit 26 outputs the content of the different performance composition 2 generated and the load information to the result display unit 29.

(Consideration of Continuous Load)

Specifically, the load distribution unit 26 acquires from the performance data DB 16 or the load DB 15 each load of each skill set for each order of the performance composition 1 and judge whether or not the load higher than the threshold value is generated. Then, if the load higher than the threshold value is continuously generated, the load distribution unit 26 changes the order of the skills so that the load higher than the threshold value is not generated continuously, within the forgoing scoring rules that stipulate the group to perform first or the group to perform last.

Figure 11:
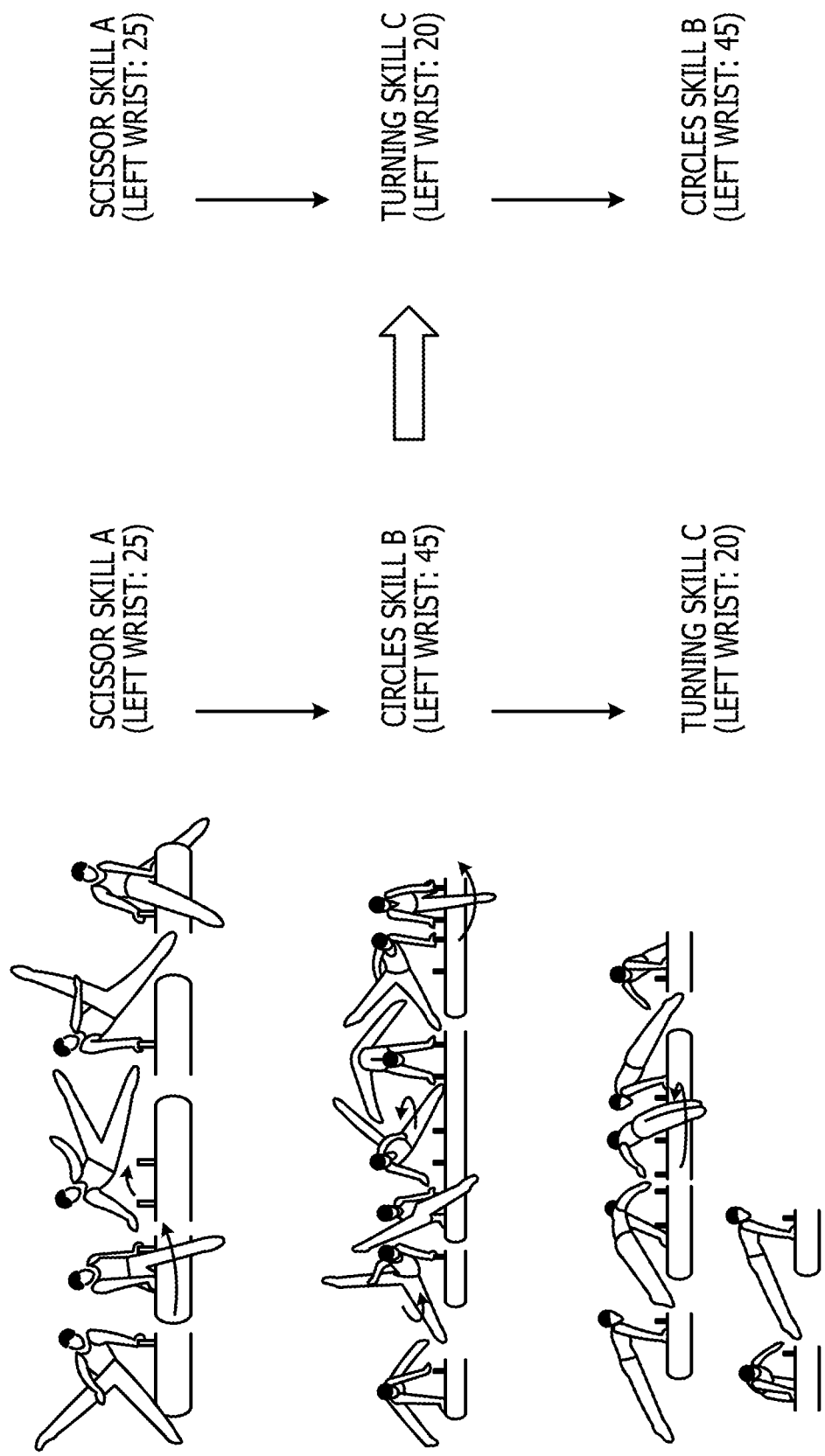
FIG. 11 is a diagram of a generation example of the performance composition that distributes the load by changing skills.

FIG. 11 is a diagram of a generation example of the performance composition that distributes the load by changing the skills. As illustrated in FIG. 11, when the order of the inputted performance composition 1 is the scissor skill A, the circles skill B, and the turning skill C, the load distribution unit 26 identifies a transition of the load on the left wrist is 25, 45, and 20. Here, since the predefined threshold value (25, for example) continues, the load distribution unit 26 switches the circles skill B and the turning skill C to generate the performance composition 2 with the order of which is the scissor skill A, the turning skill C, and the circles skill B. As a result, since the load distribution unit 26 may change the transition of the load of the left wrist to 25, 20, and 45, the load distribution unit 26 may distribute the load.

(Consideration of the Connection Action)

In addition, the load distribution unit 26 generates the performance composition 2 by changing the order of the respective skills of the inputted performance composition 1 so that the number of the connection actions is reduced. Specifically, the load distribution unit 26 refers to the connection action DB 17 and identifies the connection action performed in the inputted performance composition 1 and the load of the connection action, the connection action DB 17 storing the load of the connection action performed by the performer when the performer shifts from the first skill to the second skill. Then, the load distribution unit 26 generates the different performance composition 2 in which the performance order of the skills included in the performance composition 1 is changed and the connection action with the load smaller than the load of the identified connection action is performed.

For example, the load distribution unit 26 searches the connection action DB 17 with the skill name of the order 1 of the inputted performance composition 1 and the skill name of the order 2 as keys, and searches for the corresponding connection action. In this manner, the load distribution unit 26 identifies the connection action to occur in the performance composition 1 and identifies the load of the identified connection action from the connection action DB 17.

Furthermore, the load distribution unit 26 identifies the posture (starting and ending) of each of the skills in the performance composition 1 from the performance data DB 16. Then, the load distribution unit 26 changes the order of the skills on the condition that the ending posture of the preceding skill matches the starting posture of the following skill. At this time, the load distribution unit 26 changes the order of the skills so that the number of the identified connection actions is reduced from the original performance composition 1 or that the connection action has the smaller load than the connection action identified in the original performance composition 1.

Figure 12:
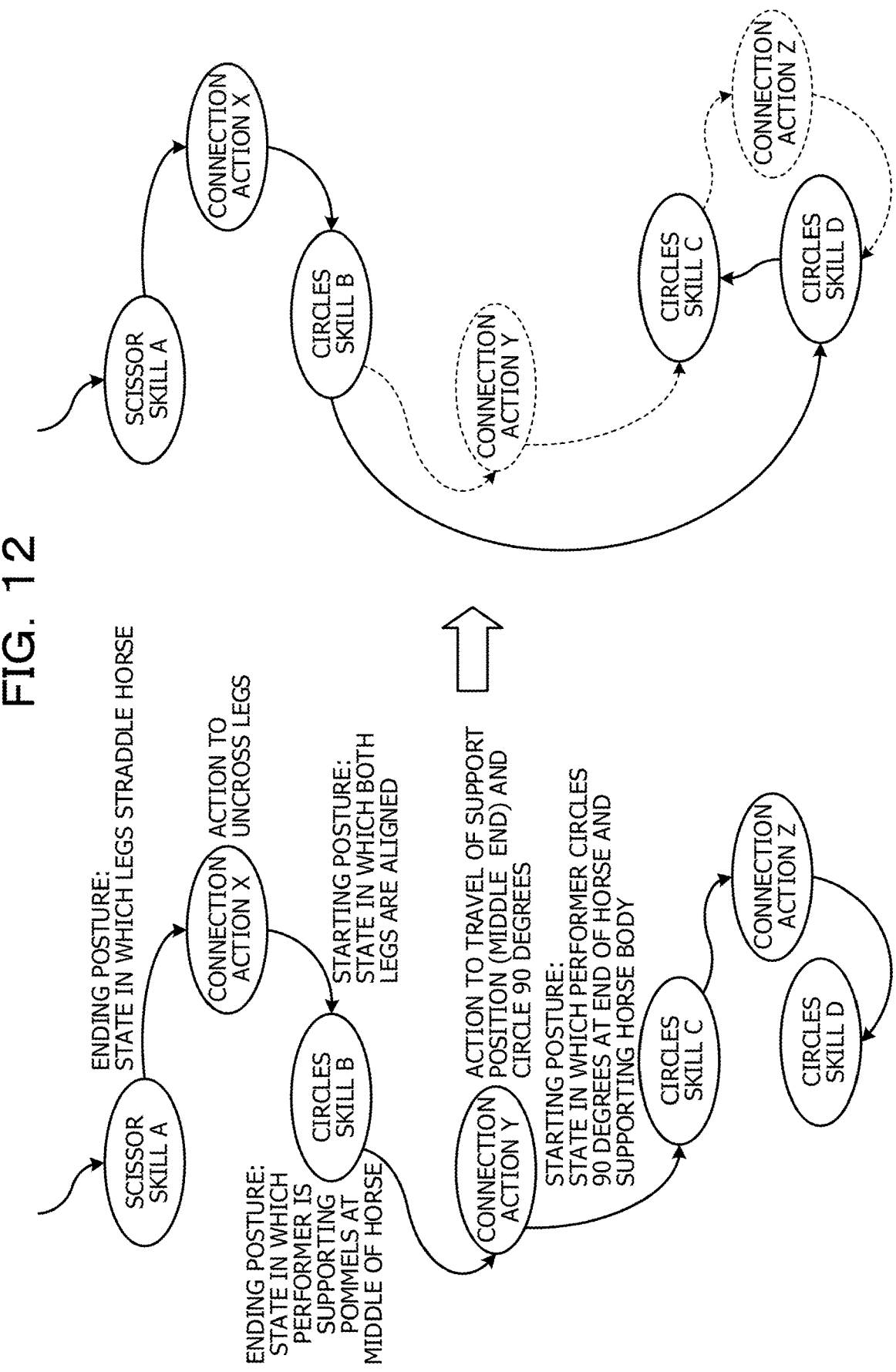
FIG. 12 is an explanatory diagram of a generation example of the performance composition that reduces a connection action to distribute the load.

FIG. 12 is an explanatory diagram of a generation example of the performance composition that reduces the connection action to distribute the load. As illustrated in FIG. 12, the load distribution unit 26 refers to the connection action DB 17 and identifies for the original performance composition 1 that the performance is performed in the order of the "Scissor Skill A, Connection Action X, circles Skill B, Connection Action Y, circles Skill C, Connection Action Z, and circles Skill D". In addition, the load distribution unit 26 identifies that the ending posture of the Scissor Skill A is "a state in which the legs straddle the horse", that the starting posture of the circles Skill B is "the state in which both legs are aligned" and the ending posture is "the state in which the performer is supporting the pommels at the middle of the horse", the starting posture of the circles Skill C is "the state in which the performer circles 90 degrees at the end of the horse and supporting the horse body", that starting posture of the circles Skill D is "the state in which the performer is supporting the pommels at the middle of the horse" and the ending posture is "the state in which the performer circles 90 degrees at the end of the horse and supporting the horse body".

Note that the Connection Action X is an action to shift from the Scissor Skill A to the circles Skill B, and is an action to uncross the legs. The Connection Action Y is an action for shifting from the circles Skill B to the circles Skill C, and is an action to move a support position from the middle to the end and to swing 90 degrees. Similarly, the Connection Action Z is an action to shift from the circles Skill C to the circles Skill D. The content of these actions may be stored in the connection action DB 17 and may be identified from the posture of the last and next skills.

For such performances, the load distribution unit 26 identifies that the ending posture of the circles Skill B "the state in which the performer is supporting the pommels at the middle of the horse" matches the starting posture of the circles Skill D "the state in which the performer is supporting the pommels at the middle of the horse". More specifically, the load distribution unit 26 judges that no connection action occurs if the performer performs the circles Skill D following the circles Skill B.

Furthermore, the load distribution unit 26 identifies that the ending posture of the circles Skill D "the state in which the performer circles 90 degrees at the end of the horse and supporting the horse body" matches the starting posture of the circles Skill C "the state in which the performer circles 90 degrees at the end of the horse and supporting the horse body". More specifically, the load distribution unit 26 judges that no connection action occurs if the performer performs the circles Skill C following the circles Skill D.

As a result, as illustrated in the right figure of FIG. 12, the load distribution unit 26 switches the circles Skill C and the circles Skill D and generates the performance composition 2 with the order of the "Scissor Skill A, Connection Action X, circles Skill B, circles Skill D, and circles Skill C". More specifically, the load distribution unit 26 may alleviate the load because the load distribution unit 26 generates the performance composition 2 in which the two connection actions are reduced, while maintaining the score of the inputted performance composition 1.

Note that even though an end state of the circles Skill D targeted for switching does not match a starting state of the circles Skill C that is performed after the circles Skill D due to the switching and another connection action is generated, the load distribution unit 26 switches the circles Skill C and the circles Skill D as far as the load of the entire performance is made smaller.

Turning back to FIG. 2, the success rate improvement unit 27 is the processing unit that generates different performance composition 2 that has the same score as the inputted performance composition 1 and includes the skill with the high success rate. Specifically, for the skills specified for the respective orders in the performance composition 1, the success rate improvement unit 27 searches the performance data DB 16 for whether or not there is any skill that belongs to the same group and whose difficulty added point is higher than the difficulty added point of the originally specified skill and whose success rate is high. Then, if the corresponding skill is searched, the success rate improvement unit 27 generates the different performance composition 2 in which the skill is replaced by the searched skill.

For example, the success rate improvement unit 27 detects the presence of "XXX handstand" belonging to Group I of the Back Scissor to Handstand of the order 1 and having the success rate higher than the Back Scissor to Handstand, of the skills having the difficulty D or higher of the Back Scissor to Handstand. Then, the success rate improvement unit 27 generates the performance composition 2 in which the Back Scissor to Handstand of the order 1 is changed to the "XXX handstand". Thereafter, similarly to the load minimization unit 25, the success rate improvement unit 27 outputs the contents, the load information, the success rate or the like of the generated performance composition 2 to the result display unit 29.

Note that if for one order, a plurality of different skills having the higher success rate is detected, the success rate improvement unit 27 may select the skill having the highest success rate or any skill. In addition, if the different skills having the higher success rate are detected in the plurality of orders in the one performance composition 1, the success rate improvement unit 27 may change the detected skills of all of the orders, may change any number of the skills, or may select and change so that the load is smaller than the predefined threshold value.

Figure 13:
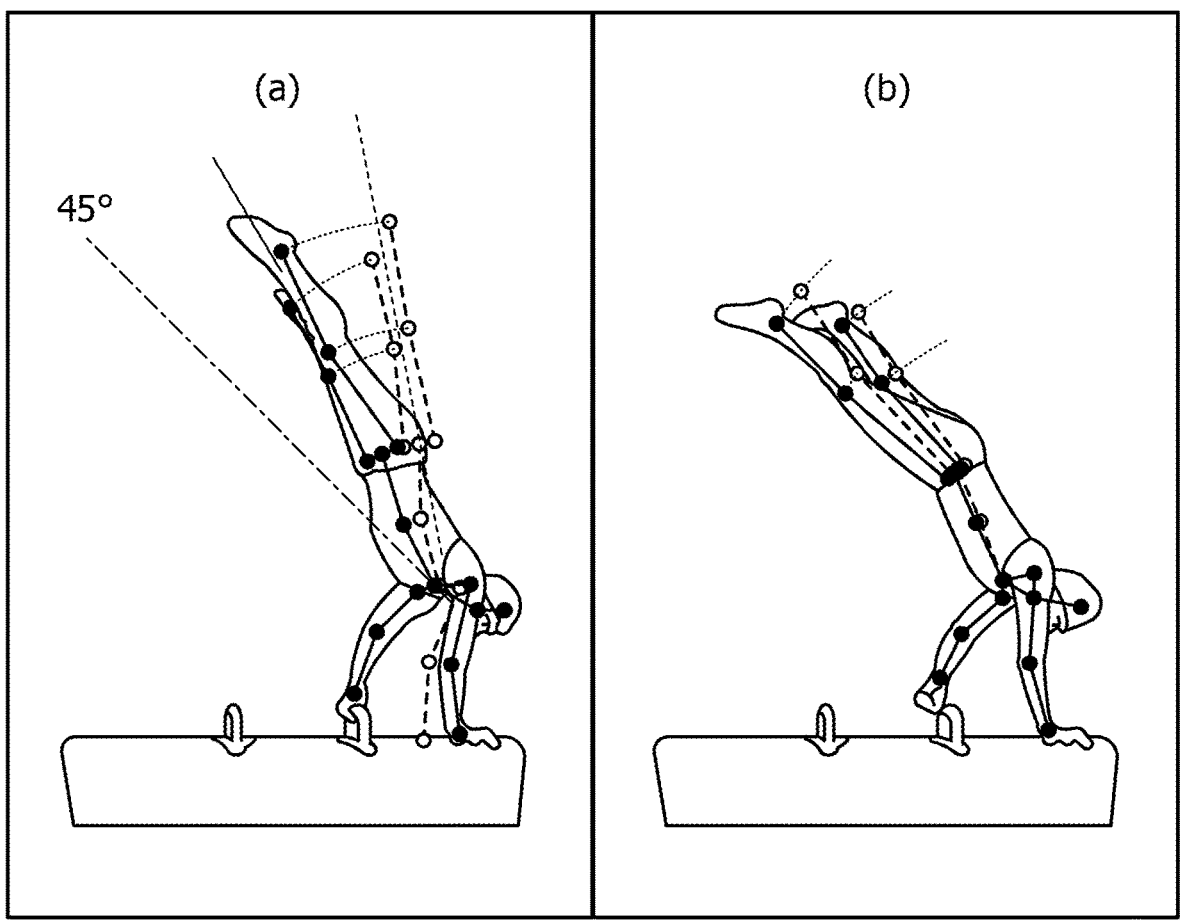
FIG. 13 is an explanatory diagram of identification of a skill with a high success rate.

Here, description is given of a judgment example of judging the skill with the high success rate. FIG. 13 is an explanatory diagram of identification of the skill with the high success rate. A solid line in FIG. 13 represents a skeleton state in which the performer successfully performed the same skill in the past, and a dotted line represents a joint angle when the performer performs the same skill recently. The success rate improvement unit 27 compares the position or the angle of each joint with a time sequence and adds weight to the skill with a small difference from the time sequence. FIG. 13(*a*) associates the weight smaller than 1 such as 0.8, because a ratio of the solid line overlapping the dotted line does not exceed a predefined threshold value, and the number of overlapping joints also does not exceed the predefined threshold value. On the other hand, FIG. 13(*b*) associates the weight larger than 1 such as 1.5, because the ratio of the solid line overlapping the dotted line is larger than the predefined threshold value and the number of overlapping joints is also larger than the predefined threshold value.

In this manner, the success rate improvement unit 27 determines the weight from the past record. As a result, even if the success rate is not calculated, the success rate improvement unit 27 may identify the skill that is likely to succeed. Moreover, even if the plurality of skills with the same success rate is detected, the success rate improvement unit 27 may identify the skill having the same success rate but with higher possibility of success, by using an approach of FIG. 13. In more detail, the success rate improvement unit 27 multiples the success rate by the weight mentioned above and selects the skill with the largest multiplication result.

Furthermore, by using the approach of FIG. 13 for each of the skills included in the performance composition 1, the success rate improvement unit 27 may display a comparison result of the past performance like FIG. 13 and recent performances. As a result, since the success rate improvement unit 27 may provide the performer with objective data on the performance, the performer may incorporate in the performance composition the skill performance of which is more approximate to the successful skill, thereby improving the possibility of the success of the entire performance. In addition, the performer may also make use of the objective data in reconstructing the performing composition, or the like. Note that a skeleton state of when the performer successfully performs the same skill as the past or the joint angle of when the performer performs the same skill recently may be acquired through the 3D sensing by the preprocessing unit 21.

The score improvement unit 28 is the processing unit that generates performance composition 2 leading to the higher score than the inputted performance composition 1. Specifically, the score improvement unit 28 generates the performance composition 2 in which the skill specified for each of the orders in the performance composition 1 is replaced by the skill that belongs to the same group and whose difficulty added point is higher than the difficulty added point of the originally specified skill.

In addition, for the order of the skills specified in the performance composition 1, the score improvement unit 28 refers to the scoring rules or the like and generates the performance composition 2 in which the order of performing the skills is changed. For example, for the skill group, if Groups I, IV, and V are specified in the performance composition group 1 but the rule is present that the order of Groups I, V, and IV is given more added points, the score improvement unit 28 generates the performance composition 2 in which the order is changed to Groups I, V, and IV. Then, similarly to the load minimization unit 25, the score improvement unit 28 outputs the contents or changes in the score information or the like of the generated performance composition 2 to the result display unit 29.

The result display unit 29 is the processing unit that receives various types of information from the load minimization unit 25, the load distribution unit 26, the success rate improvement unit 27, and the score improvement unit 28, and displays an improvement result. Specifically, the result display unit 29 generates and displays a result screen including the order of performances, the load information, the scores, changed parts or the like, for each performance composition 2 generated by each of the load minimization unit 25, the load distribution unit 26, the success rate improvement unit 27, and the score improvement unit 28.

Figure 14:
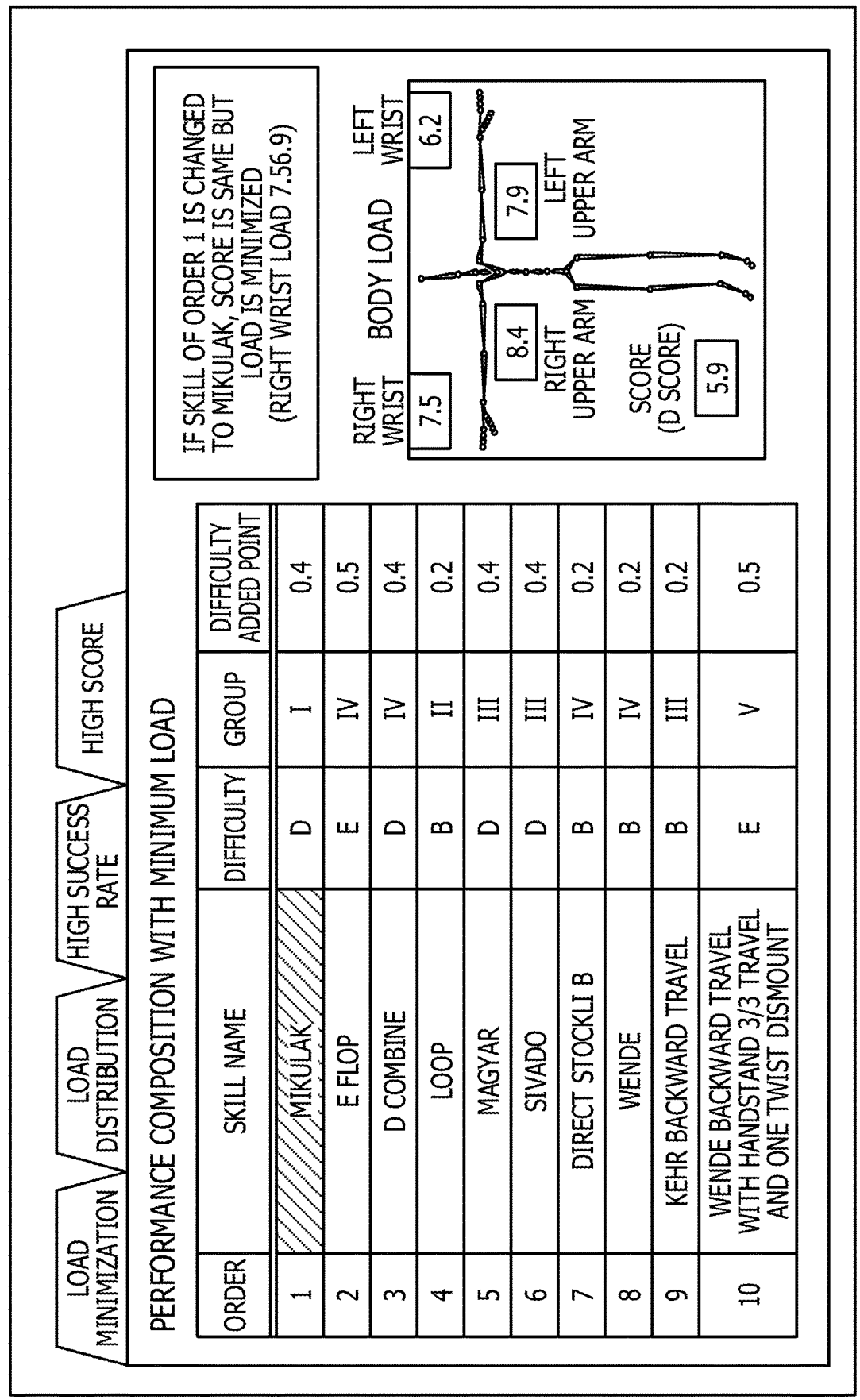
FIG. 14 is an explanatory diagram of an example of a screen that displays an improvement result.

FIG. 14 is an explanatory diagram of an example of a screen that displays the improvement result. As illustrated in FIG. 14, the result display unit 29 generates the screen on which are set tabs corresponding to each of the load minimization unit 25, the load distribution unit 26, the success rate improvement unit 27, and the score improvement unit 28, and switches a display screen depending on selection of the tab. The screen to be switched by the tab displays a performance composition table including the order, the difficulty, the group, and the difficulty added point of the performance composition 2 that is generated as the improvement proposal, the total load of the entire performance composition 2, the load by the skill, the contents changed from the performance composition 1, or the like.

Here, FIG. 14 illustrates, by way of example, the performance composition with the minimum load. When receiving from the load minimization unit 25 various types of information related to the performance composition 2 generated by the load minimization unit 25, the result display unit 29 generates the screen illustrated in FIG. 14. Specifically, the result display unit 29 displays the result screen including the table of the performance composition 2 in which the "Order 1, Mikulak", which is changed from the original performance composition 1, is highlighted, the changed content "If the skill of the order 1 is changed to Mikulak, the score is same but the load is minimized", the changed load information "Load on the right wrist 7.5→6.9", and the body load. Note that for the body load, the load of the entire performance composition 2 may be displayed or the load of the skill selected in the table of the performance composition 2 may be displayed. Note that when the load distribution tag is selected, the result display unit 29 displays the improvement proposal of the load distribution unit 26. When the high success rate tag is selected, the result display unit 29 displays the improvement proposal of the success rate improvement unit 27, and when the high score tag is selected, the result display unit 29 displays the improvement proposal of the score improvement unit 28.

[Flow of Processing]

Figure 15:
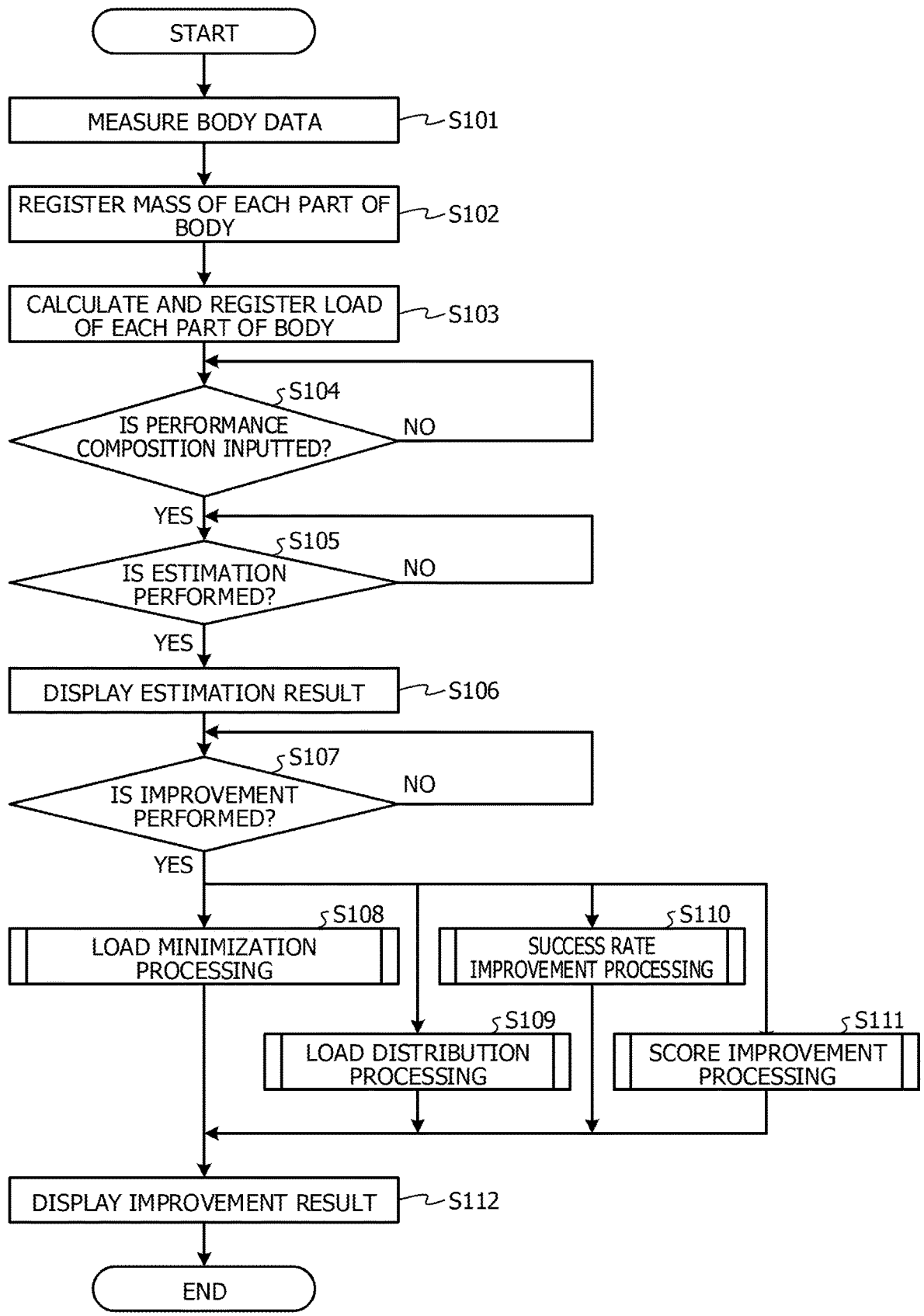
FIG. 15 is a flow chart illustrating flow of processing.

FIG. 15 is a flow chart illustrating flow of processing. As illustrated in FIG. 15, the preprocessing unit 21 measures body data using the 3D scanner or the like (S101), measures and registers the mass of each part of the body by the 3D sensing or the like (S102), and calculates and registers the load of each part of the body for each of the skills using the information (S103).

Subsequently, when the performance composition reception unit 22 receives the input of the performance composition (S104: Yes), the estimation unit 23 judges whether or not an instruction to perform the estimation is given (S105). Then, if the instruction to perform the estimation is given (S105: Yes), the estimation unit 23 estimates the score or the load and displays the estimation result (S106).

Thereafter, if the improvement execution unit 24 is instructed to perform improvement (S107: Yes), the improvement execution unit 24 performs the processing from S108 to S111 concurrently.

More specifically, the load minimization unit 25 performs load minimization processing to generate the performance composition 2 of the improvement proposal that minimizes the load (S108). Specifically, the load minimization unit 25 generates the different performance composition 2 according to the scoring rules, the performance composition 2 leading to the score higher than the performance score of the performance composition 1 and reducing the total load of the performance composition 1.

In addition, the load distribution unit 26 performs load distribution processing to generate the performance composition 2 of the improvement proposal that distributes the load (S109). Specifically, the load distribution unit 26 changes the order of the respective skills in the inputted performance composition 1 to generate the performance composition 2, so that the parts the load on which is continuously high is reduced. For example, the load distribution unit 26 consider the continuous load and the connection action described above to generate the performance composition 2.

In addition, the success rate improvement unit 27 performs success rate improvement processing to generate the performance composition 2 of the improvement proposal that increases the success rate (S110). Specifically, the success rate improvement unit 27 generates the different performance composition 2 that includes the skill having the same score as the inputted performance composition 1 and the high success rate.

In addition, the score improvement unit 28 performs score improvement processing to generate the performance composition 2 of the improvement proposal that increases the score (S111). Specifically, the score improvement unit 28 generates the performance composition 2 in which the performance specified for each of the orders in the performance composition 1 is replaced by the skill that belongs to the same group and has the difficulty added point higher than the difficulty added point of the originally specified skill.

Then, the result display unit 29 displays the improvement results including the respective improvement proposals obtained from S108 to S111 (S112).

[Effects]

As described above, the measurement device 10 may assist the performance composition that alleviates the burdens on the body. In addition, considering the load applied on the joints when the skill is actually performed, based on the body characteristics of individual persons, the measurement device 10 may select the performance composition that has the high past success rate and makes it possible to acquire the highest score. Moreover, the measurement device 10 may display each performance in progress and how the load on the joint (part) changes. Even if the complicated marking results are updated, the measurement device 10 may also propose the improvement proposal that follows the updates and observes the scoring rules.

Embodiment 2

Although the embodiment of the present invention is described above, the present invention may also be practiced in various different modes other than the foregoing embodiment. Thus, different embodiments are described below.

[Improvement Processing]

Although description is given of the example in which the four load minimization processing, load distribution processing, success rate improvement processing, and score improvement processing are performed concurrently in the foregoing embodiment, the present invention is not limited to the foregoing embodiment, and may include one or any combination thereof or may be changed in the setting in any manner.

[Body Information and Performance Information]

In the foregoing embodiment, although description is given of the example that uses the 3D scanner or the 3D sensing, the embodiment is merely an example, and is not limited thereto. For example, if image analysis or standard information of the same physical constitution is used, the foregoing improvement proposal may still be generated. In addition, the load or the mass of the part may be a measurement results itself. Numerical values of the measurement result based on a predefined standard or weight or the like obtained from a comparison of a standard value and the measurement result may be similarly processed.

[Hardware Configuration]

Figure 16:
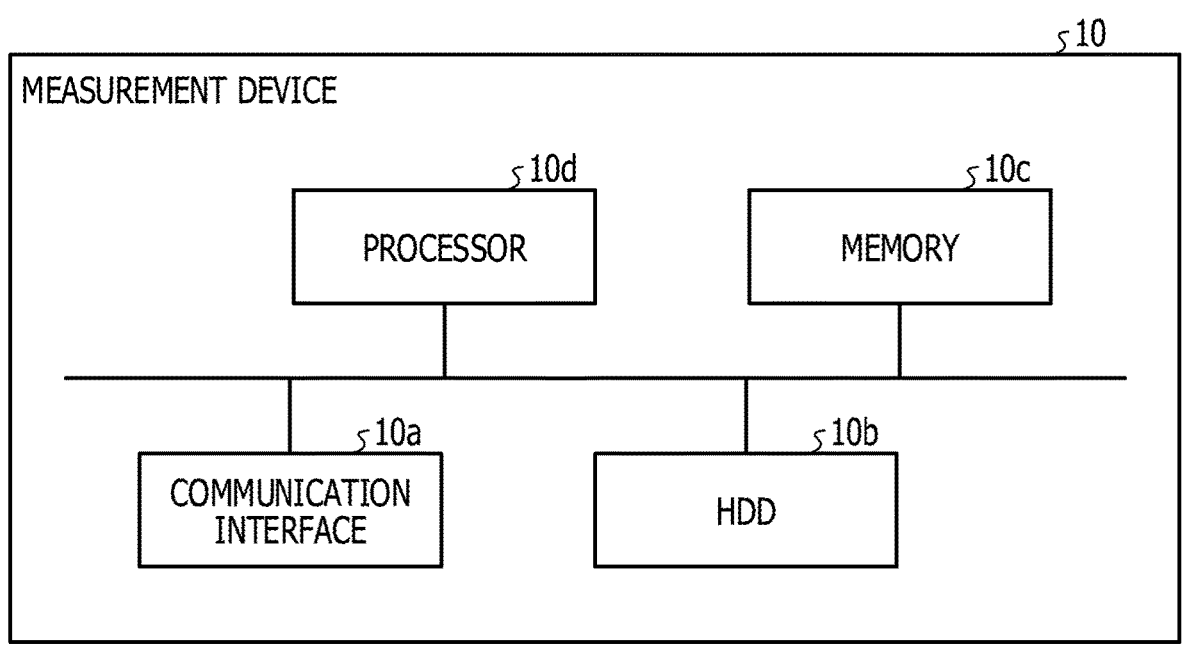
FIG. 16 is a diagram of a hardware configuration example.

FIG. 16 is a diagram of a hardware configuration example. As illustrated in FIG. 16, the measurement device 10 includes a communication interface 10a, an HDD (Hard Disk Drive) 10b, a memory 10c, and a processor 10d.

The communication interface 10a is a network interface card or the like that controls communications of other devices. The HDD 10b is an example of a storage device that stores a program or data or the like.

Examples of the memory 10c include a RAM (Random Access Memory) such as an SDRAM (Synchronous Dynamic Random Access Memory), a ROM (Read Only Memory), a flash memory or the like. Examples of the processor 10d includes a CPU (Central Processing Unit), a DSP (Digital Signal Processor), an FPGA (Field Programmable Gate Array), a PLD (Programmable Logic Device), or the like.

In addition, the measurement device 10 acts as an information processor that performs a measurement method by reading and executing a program. More specifically, the measurement device 10 executes the program that performs similar functions to the preprocessing unit 21, the performance composition reception unit 22, the estimation unit 23, the improvement execution unit 24, and the result display unit 29. Consequently, the measurement device 10 may perform a process that performs similar functions to the preprocessing unit 21, the performance composition reception unit 22, the estimation unit 23, the improvement execution unit 24, and the result display unit 29. Note that the program referred to in this other embodiment is not limited to being executed by the measurement device 10. For example, the present disclosure may be similarly applicable if other computer or server executes the program or if the other computer and server execute the program in cooperation.

The program may be distributed through a network such as Internet. In addition, the program may be stored in a computer-readable storage medium such as a hard disk, a flexible disk (FD), a CD-ROM, an MO (Magneto-Optical disk), a DVD (Digital Versatile Disc) or the like and may be executed by being read from the storage medium by the computer.

[System]

In addition, in each processing described in the embodiment, all or some of the processing that is described as being automatically performed may be manually performed. Alternatively, all or some of the processing that is described as being manually performed may be automatically performed with a publicly known method. In addition to this, information including the processing procedure, the control procedure, the specific names, and the various types of data or parameters described in the foregoing document or illustrated in the drawings may be changed arbitrarily, unless otherwise specified.

In addition, each component of each device illustrated is functionally conceptual, and is not desirably configured physically as illustrated. More specifically, specific forms of distribution and integration of each device are not limited to the illustrated distribution and integration. That is, all or some of the forms may be distributed or integrated functionally or physical in any unit, depending on various types of loads or usage or the like. Moreover, some or all of each processing function performed by each device is implemented by the CPU or a program that is analyzed and executed by the CPU, or may be implemented as hardware by a wired logic.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A generation device comprising:
a processor configured to obtain load information by sensing a performer, the load information indicating a plurality of loads applied to a body for each of a plurality of skills, the plurality of loads respectively corresponding to each of a plurality of parts of the body;
a memory configured to store the load information, and the processor is further configured to:
receive first performance composition including a plurality of skills;
specify a first load value based on the load information, the first load value indicating a total of the load applied to the performer who performs the first performance composition,
display the specified first load value,
determine whether or not an instruction to perform improvement is received in response to the displayed first load value,
when it is determined that the instruction is received, refer to scoring rules that stipulate scores based on difficulty of skills and specify a first performance score indicating a total of scores of the plurality of skills included in the first performance composition,
based on the load information and the scoring rules, generate second performance composition according to performance rules that stipulate composition of the skills, the second performance composition leading to a second performance score higher than the first performance score and being able to perform a second load value lower than the first load value, and
display the generated second performance composition, wherein,
the second load value indicating a total of the load applied to the performer who performs the second performance composition, and
the second performance score indicating a total of scores of a plurality of skills included in the second performance composition.

2. The generation device according to claim 1, the processor further configured to:
refer to connection action information representing a load of a connection action to be performed by a performer when the performer shifts from a first skill to a second skill and identify the connection action performed in the first performance composition and the load of the connection action; and
change performance order of the plurality of skills included in the first performance composition and generate third performance composition which includes a connection action having a smaller load than the load of the identified connection action.

3. The generation device according to claim 1, the processor further configured to:
refer to the load information and identify the load of each body part, for each of the plurality of skills included in the first performance composition; and
if there is a body part on which the load higher than a threshold value is continuously applied, generate third performance composition in which the performance order of the plurality of skills included in the first performance composition is changed and the load higher than the threshold value does not continue on the body part.

4. The generation device according to claim 1, the processor further configured to:
for each of the plurality of skills included in the first performance composition, if there is another skill having a score higher than the score of the skill set in the first performance composition and a high past success rate, generate third performance composition in which the skill set in the first performance composition is replaced by the other skill.

5. The generation device according to claim 1, the processor further configured to:
perform the processing to generate third performance composition in which each of the plurality of skills included in the first performance composition is replaced by a skill having a score higher than the score of the skill set in the first performance composition, or to refer to point addition information that associates the performance order of the skills with the point addition and generate third performance composition in which the performance order is changed to have a score higher than the score of the performance order of the plurality of skills set in the first performance composition.

6. A generation method executed by a processor, the generation method comprising:
obtaining load information by sensing a performer, the load information indicating a plurality of loads applied to a body for each of a plurality of skills, the plurality of loads respectively corresponding to each of a plurality of parts of the body;
storing the load information;
receiving first performance composition including a plurality of skills;
specifying a first load value based on the load information, the first load value indicating a total of the load applied on the performer who performs the first performance composition;
displaying the specified first load value;
determining whether or not an instruction to perform improvement is received in response to the displayed first load value;
when it is determined that the instruction is received, referring to scoring rules that stipulate scores based on difficulty of skills and specifies a first performance score indicating a total of scores of the plurality of skills included in the first performance composition;
based on the load information and the scoring rules, generating second performance composition according to performance rules that stipulate composition of skills, the second performance composition leading to a second performance score higher than the first performance score and being able to perform a second load value lower than the first load value, and
displaying the generated second performance composition, wherein,
the second load value indicating a total of the load applied to the performer who performs the second performance composition, and
the second performance score indicating a total of scores of a plurality of skills included in the second performance composition.

7. The generation method according to claim 6, further comprising:
referring to connection action information representing a load of a connection action to be performed by a performer when the performer shifts from a first skill to a second skill and identify the connection action performed in the first performance composition and the load of the connection action; and
changing performance order of the plurality of skills included in the first performance composition and generate third performance composition which includes a connection action having a smaller load than the load of the identified connection action.

8. The generation method according to claim 6, further comprising:
referring to the load information and identify the load of each body part, for each of the plurality of skills included in the first performance composition; and
if there is a body part on which the load higher than a threshold value is continuously applied, generating third performance composition in which the performance order of the plurality of skills included in the first performance composition is changed and the load higher than the threshold value does not continue on the body part.

9. The generation method according to claim 6, further comprising:
for each of the plurality of skills included in the first performance composition, if there is another skill having a score higher than the score of the skill set in the first performance composition and a high past success rate, generating third performance composition in which the skill set in the first performance composition is replaced by the other skill.

10. The generation method according to claim 6, further comprising:
generating third performance composition in which each of the plurality of skills included in the first performance composition is replaced by a skill having a score higher than the score of the skill set in the first performance composition, or to refer to point addition information that associates the performance order of the skills with the point addition and
generating third performance composition in which the performance order is changed to have a score higher than the score of the performance order of the plurality of skills set in the first performance composition.

11. A non-transitory computer-readable storage medium storing a generation program that causes a processor to execute a process, the process comprising:
obtaining load information by sensing a performer, the load information indicating a plurality of loads applied to a body for each of a plurality of skills, the plurality of loads respectively corresponding to each of a plurality of parts of the body;
storing the load information;
receiving first performance composition including a plurality of skills;
specifying a first load value based on the load information, the first load value indicating a total of the load applied on the performer who performs the first performance composition;
displaying the specified first load value;
determining whether or not an instruction to perform improvement is received in response to the displayed first load value;
when it is determined that the instruction is received, referring to scoring rules that stipulate scores based on difficulty of skills and specifies a first performance score indicating a total of scores of the plurality of skills included in the first performance composition;
based on the load information and the scoring rules, generating second performance composition according to performance rules that stipulate composition of skills, the second performance composition leading to a second performance score higher than the first performance score and being able to perform a second load value lower than the first load value, and
displaying the generated second performance composition, wherein,
the second load value indicating a total of the load applied to the performer who performs the second performance composition, and
the second performance score indicating a total of scores of a plurality of skills included in the second performance composition.

12. The non-transitory computer-readable storage medium according to claim 11, the process further comprising:
referring to connection action information representing a load of a connection action to be performed by a performer when the performer shifts from a first skill to a second skill and identify the connection action performed in the first performance composition and the load of the connection action; and
changing performance order of the plurality of skills included in the first performance composition and generate third performance composition which includes a connection action having a smaller load than the load of the identified connection action.

13. The non-transitory computer-readable storage medium according to claim 11, the process further comprising:
referring to the load information and identify the load of each body part, for each of the plurality of skills included in the first performance composition; and
if there is a body part on which the load higher than a threshold value is continuously applied, generating third performance composition in which the performance order of the plurality of skills included in the first performance composition is changed and the load higher than the threshold value does not continue on the body part.

14. The non-transitory computer-readable storage medium according to claim 11, the process further comprising:
for each of the plurality of skills included in the first performance composition, if there is another skill having a score higher than the score of the skill set in the first performance composition and a high past success rate, generating third performance composition in which the skill set in the first performance composition is replaced by the other skill.

15. The non-transitory computer-readable storage medium according to claim 11, the process further comprising:
generating third performance composition in which each of the plurality of skills included in the first performance composition is replaced by a skill having a score higher than the score of the skill set in the first performance composition, or to refer to point addition information that associates the performance order of the skills with the point addition and
generating third performance composition in which the performance order is changed to have a score higher than the score of the performance order of the plurality of skills set in the first performance composition.

* * * * *